US009089358B2

(12) United States Patent
Emanuel

(10) Patent No.: US 9,089,358 B2
(45) Date of Patent: *Jul. 28, 2015

(54) SURGICAL CUTTING DEVICE AND METHOD FOR ITS USE

(71) Applicant: Smith & Nephew, Inc., Memphis, TN (US)

(72) Inventor: Mark Hans Emanuel, Bioemendaal (NL)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/081,801

(22) Filed: Nov. 15, 2013

(65) Prior Publication Data

US 2014/0074136 A1 Mar. 13, 2014

Related U.S. Application Data

(60) Continuation of application No. 11/929,940, filed on Oct. 30, 2007, which is a division of application No. 11/780,759, filed on Jul. 20, 2007, now Pat. No. 8,061,359, which is a continuation of application No. 09/486,977, filed as application No. PCT/NL98/00504 on Sep. 4, 1998, now Pat. No. 7,249,602.

(30) Foreign Application Priority Data

Sep. 4, 1997 (NL) .................................... 1006944

(51) Int. Cl.
*A61B 1/00* (2006.01)
*A61B 17/32* (2006.01)
(Continued)

(52) U.S. Cl.
CPC ......... *A61B 17/320016* (2013.01); *A61B 1/018* (2013.01); *A61B 17/32002* (2013.01); *A61B 1/12* (2013.01); *A61B 19/5212* (2013.01); *A61B 2017/4216* (2013.01); *A61B 2217/005* (2013.01); *A61B 2217/007* (2013.01)

(58) Field of Classification Search
USPC ............. 600/104–105, 118, 153–159; 606/46
See application file for complete search history.

(56) References Cited

U.S. PATENT DOCUMENTS

| 1,585,934 A | 5/1926 | Muir |
| 1,666,332 A | 4/1928 | Hirsch |
| 1,831,786 A | 11/1931 | Duncan |

(Continued)

FOREIGN PATENT DOCUMENTS

| DE | 3339322 A1 | 5/1984 |
| DE | 3206381 C2 | 7/1986 |

(Continued)

OTHER PUBLICATIONS

ACMI Corporation, "Dolphin II Hysteroscopic Fluid Management Systems," ACMI Corporation, 2002 (1 page).

(Continued)

*Primary Examiner* — Matthew J Kasztejna
(74) *Attorney, Agent, or Firm* — Nixon Peabody LLP

(57) ABSTRACT

A surgical endoscopic cutting device includes cutting elements fitted in a protective tube. The device has an inlet for fluid, a discharge outlet for tissue and fluid, and a further outlet that discharges most of the fluid.

26 Claims, 3 Drawing Sheets

(51) Int. Cl.
*A61B 1/018* (2006.01)
*A61B 1/12* (2006.01)
*A61B 19/00* (2006.01)
*A61B 17/42* (2006.01)

(56) References Cited

U.S. PATENT DOCUMENTS

| | | |
|---|---|---|
| 2,708,437 A | 5/1955 | Hutchins et al. |
| 3,297,022 A | 1/1967 | Wallace |
| 3,686,706 A | 8/1972 | Finley |
| 3,734,099 A | 5/1973 | Bender et al. |
| 3,791,379 A * | 2/1974 | Storz ................. 600/158 |
| 3,812,855 A | 5/1974 | Banko |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent |
| 4,261,346 A | 4/1981 | Wettermann |
| 4,294,234 A | 10/1981 | Matsuo |
| 4,316,465 A | 2/1982 | Dotson, Jr. |
| 4,369,768 A * | 1/1983 | Vukovic ................. 600/123 |
| 4,392,485 A * | 7/1983 | Hiltebrandt ............ 600/153 |
| 4,414,962 A * | 11/1983 | Carson ..................... 600/138 |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A * | 7/1986 | Arakawa et al. ............. 600/112 |
| 4,601,290 A | 7/1986 | Effron et al. |
| 4,606,330 A * | 8/1986 | Bonnet ..................... 607/128 |
| 4,630,598 A | 12/1986 | Bonnet |
| 4,644,952 A | 2/1987 | Patipa et al. |
| 4,649,919 A | 3/1987 | Thimsen et al. |
| 4,700,694 A * | 10/1987 | Shishido ................. 600/104 |
| 4,706,656 A * | 11/1987 | Kuboto ..................... 600/153 |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A * | 8/1990 | Sachse et al. ................. 606/170 |
| 4,955,882 A | 9/1990 | Hakky |
| 4,986,827 A | 1/1991 | Akkas et al. |
| 4,998,527 A * | 3/1991 | Meyer ..................... 600/104 |
| 4,998,914 A | 3/1991 | Wiest et al. |
| 5,007,917 A | 4/1991 | Evans |
| 5,027,792 A * | 7/1991 | Meyer ..................... 600/104 |
| 5,037,386 A * | 8/1991 | Marcus et al. ................. 604/43 |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A * | 12/1992 | Sakashita et al. ................. 606/27 |
| 5,176,677 A * | 1/1993 | Wuchinich ..................... 606/46 |
| 5,195,541 A * | 3/1993 | Obenchain ..................... 128/898 |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A * | 5/1994 | Hakky et al. ..................... 606/15 |
| 5,312,425 A | 5/1994 | Evans et al. |
| 5,312,430 A * | 5/1994 | Rosenbluth et al. .......... 606/192 |
| 5,320,091 A * | 6/1994 | Grossi et al. ................. 600/104 |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,411,513 A | 5/1995 | Ireland et al. |
| 5,425,376 A | 6/1995 | Banys et al. |
| 5,429,601 A | 7/1995 | Conley et al. |
| 5,443,476 A | 8/1995 | Shapiro |
| 5,449,356 A | 9/1995 | Walbrink et al. |
| 5,456,673 A * | 10/1995 | Ziegler et al. ................. 604/264 |
| 5,456,689 A * | 10/1995 | Kresch et al. ................. 606/180 |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A * | 6/1996 | Kresch et al. ................. 606/170 |
| 5,549,541 A * | 8/1996 | Muller ..................... 600/105 |
| 5,556,378 A | 9/1996 | Storz et al. |
| 5,563,481 A | 10/1996 | Krause |
| 5,569,164 A * | 10/1996 | Lurz ..................... 600/158 |
| 5,569,254 A * | 10/1996 | Carlson et al. ................. 606/79 |
| 5,569,284 A | 10/1996 | Young et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A * | 10/1997 | Bonnet et al. ................. 600/105 |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A * | 3/1998 | Alden et al. ................. 606/180 |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A * | 9/1998 | Chin et al. ..................... 604/65 |
| 5,810,861 A | 9/1998 | Gaber |
| 5,814,009 A | 9/1998 | Wheatman |
| 5,833,643 A | 11/1998 | Ross et al. |
| 5,840,060 A * | 11/1998 | Beiser et al. ..................... 604/66 |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |

(56) References Cited

U.S. PATENT DOCUMENTS

| | | | |
|---|---|---|---|
| 5,916,229 A | 6/1999 | Evans | |
| 5,925,055 A | 7/1999 | Adrian et al. | |
| 5,928,163 A | 7/1999 | Roberts et al. | |
| 5,944,668 A | 8/1999 | Vancaillie et al. | |
| 5,947,990 A | 9/1999 | Smith | |
| 5,951,490 A | 9/1999 | Fowler | |
| 5,956,130 A | 9/1999 | Vancaillie et al. | |
| 5,957,832 A | 9/1999 | Taylor et al. | |
| 6,001,116 A | 12/1999 | Heisler et al. | |
| 6,004,320 A | 12/1999 | Casscells et al. | |
| 6,007,513 A | 12/1999 | Anis et al. | |
| 6,024,751 A | 2/2000 | Lovato et al. | |
| 6,032,673 A * | 3/2000 | Savage et al. | 128/898 |
| 6,039,748 A | 3/2000 | Savage et al. | |
| 6,042,552 A | 3/2000 | Cornier | |
| 6,068,641 A | 5/2000 | Varsseveld | |
| 6,086,542 A | 7/2000 | Glowa et al. | |
| 6,090,094 A * | 7/2000 | Clifford et al. | 604/500 |
| 6,090,123 A | 7/2000 | Culp et al. | |
| 6,113,594 A * | 9/2000 | Savage | 606/41 |
| 6,119,973 A | 9/2000 | Galloway | |
| 6,120,147 A | 9/2000 | Vijfvinkel et al. | |
| 6,120,462 A | 9/2000 | Hibner et al. | |
| 6,132,448 A | 10/2000 | Perez et al. | |
| 6,149,633 A | 11/2000 | Maaskamp | |
| 6,156,049 A | 12/2000 | Lovato et al. | |
| 6,159,160 A * | 12/2000 | Hsei et al. | 600/560 |
| 6,159,209 A * | 12/2000 | Hakky | 606/45 |
| 6,203,518 B1 | 3/2001 | Anis et al. | |
| 6,217,543 B1 | 4/2001 | Anis et al. | |
| 6,224,603 B1 | 5/2001 | Marino | |
| 6,244,228 B1 | 6/2001 | Kuhn et al. | |
| 6,258,111 B1 | 7/2001 | Ross et al. | |
| 6,277,096 B1 | 8/2001 | Cortella et al. | |
| 6,315,714 B1 | 11/2001 | Akiba | |
| 6,358,200 B1 | 3/2002 | Grossi | |
| 6,358,263 B2 | 3/2002 | Mark et al. | |
| 6,359,200 B1 | 3/2002 | Day | |
| 6,402,701 B1 | 6/2002 | Kaplan et al. | |
| 6,428,486 B2 | 8/2002 | Ritchart et al. | |
| 6,494,892 B1 | 12/2002 | Ireland et al. | |
| 6,585,708 B1 | 7/2003 | Maaskamp | |
| 6,610,066 B2 | 8/2003 | Dinger et al. | |
| 6,626,827 B1 | 9/2003 | Felix et al. | |
| 6,632,182 B1 | 10/2003 | Treat | |
| 6,656,132 B1 | 12/2003 | Ouchi | |
| 6,712,773 B1 | 3/2004 | Viola | |
| 6,837,847 B2 | 1/2005 | Ewers et al. | |
| 7,025,732 B2 | 4/2006 | Thompson et al. | |
| 7,150,713 B2 * | 12/2006 | Shener et al. | 600/156 |
| 7,226,459 B2 | 6/2007 | Cesarini et al. | |
| 7,249,602 B1 | 7/2007 | Emanuel | |
| 7,510,563 B2 | 3/2009 | Cesarini et al. | |
| 7,763,033 B2 | 7/2010 | Gruber et al. | |
| 7,922,737 B1 | 4/2011 | Cesarini et al. | |
| 8,061,359 B2 * | 11/2011 | Emanuel | 128/898 |
| 2001/0039963 A1 | 11/2001 | Spear et al. | |
| 2001/0047183 A1 | 11/2001 | Privitera et al. | |
| 2002/0058859 A1 | 5/2002 | Brommersma | |
| 2003/0050603 A1 | 3/2003 | Todd | |
| 2003/0050638 A1 | 3/2003 | Yachia et al. | |
| 2003/0078609 A1 | 4/2003 | Finlay et al. | |
| 2003/0114875 A1 | 6/2003 | Sjostrom | |
| 2005/0043690 A1* | 2/2005 | Todd | 604/248 |
| 2005/0085692 A1 | 4/2005 | Kiehn et al. | |
| 2006/0036132 A1 | 2/2006 | Renner et al. | |
| 2006/0047185 A1 | 3/2006 | Shener et al. | |
| 2006/0241586 A1 | 10/2006 | Wilk | |
| 2008/0015621 A1* | 1/2008 | Emanuel | 606/170 |
| 2008/0058588 A1* | 3/2008 | Emanuel | 600/104 |
| 2008/0058842 A1 | 3/2008 | Emanuel | |
| 2008/0097468 A1 | 4/2008 | Adams et al. | |
| 2008/0097469 A1 | 4/2008 | Gruber et al. | |
| 2008/0097470 A1 | 4/2008 | Gruber et al. | |
| 2008/0097471 A1 | 4/2008 | Adams et al. | |
| 2008/0135053 A1 | 6/2008 | Gruber et al. | |
| 2008/0146872 A1 | 6/2008 | Gruber et al. | |
| 2008/0146873 A1 | 6/2008 | Adams et al. | |
| 2008/0245371 A1 | 10/2008 | Gruber | |
| 2008/0249366 A1 | 10/2008 | Gruber et al. | |
| 2008/0249534 A1 | 10/2008 | Gruber et al. | |
| 2008/0249553 A1 | 10/2008 | Gruber et al. | |
| 2008/0262308 A1 | 10/2008 | Prestezog et al. | |
| 2009/0270812 A1 | 10/2009 | Litscher et al. | |
| 2009/0270895 A1 | 10/2009 | Churchill et al. | |
| 2009/0270896 A1 | 10/2009 | Sullivan et al. | |
| 2009/0270897 A1 | 10/2009 | Adams et al. | |
| 2009/0270898 A1 | 10/2009 | Chin et al. | |
| 2010/0087798 A1 | 4/2010 | Adams et al. | |
| 2010/0152647 A1 | 6/2010 | Shener et al. | |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 102006022827 A1 | 12/2006 |
| EP | 0310285 A2 | 4/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 5/1997 |
| EP | 1681022 A1 | 7/2006 |
| GB | 2093353 A | 9/1982 |
| GB | 2311468 A | 10/1997 |
| JP | 01-75416 | 5/1989 |
| JP | 2003245247 A | 9/2003 |
| NL | 1006944 C2 | 3/1999 |
| WO | WO 81/01648 A1 | 6/1981 |
| WO | WO 92/11816 A2 | 7/1992 |
| WO | WO 93/07821 A1 | 4/1993 |
| WO | WO 93/15664 A1 | 8/1993 |
| WO | WO 94/26181 A1 | 11/1994 |
| WO | WO 95/05777 A1 | 3/1995 |
| WO | WO 95/10981 A1 | 4/1995 |
| WO | WO 95/10982 A1 | 4/1995 |
| WO | WO 95/22935 A1 | 8/1995 |
| WO | WO 95/30377 A1 | 11/1995 |
| WO | WO 96/11638 A1 | 4/1996 |
| WO | WO 96/26676 A1 | 9/1996 |
| WO | WO 97/09922 A1 | 3/1997 |
| WO | WO 97/17027 A1 | 5/1997 |
| WO | WO 97/19642 A1 | 6/1997 |
| WO | WO 97/24071 A1 | 7/1997 |
| WO | WO 97/34534 A1 | 9/1997 |
| WO | WO 97/35522 A1 | 10/1997 |
| WO | WO 98/09569 A1 | 3/1998 |
| WO | WO 98/10707 A1 | 3/1998 |
| WO | WO 98/46147 A1 | 10/1998 |
| WO | WO 99/03407 A1 | 1/1999 |
| WO | WO 99/03409 A1 | 1/1999 |
| WO | WO 99/07295 A1 | 2/1999 |
| WO | WO 99/11184 A1 | 3/1999 |
| WO | WO 99/39648 A1 | 8/1999 |
| WO | WO 99/44506 A1 | 9/1999 |
| WO | WO 99/60935 A1 | 12/1999 |
| WO | WO 00/12010 A1 | 3/2000 |
| WO | WO 00/28890 A1 | 5/2000 |
| WO | WO 00/33743 A1 | 6/2000 |
| WO | WO 00/44295 A1 | 8/2000 |
| WO | WO 00/47116 A1 | 8/2000 |
| WO | WO 00/57797 A1 | 10/2000 |
| WO | WO 01/35831 A1 | 5/2001 |
| WO | WO 01/58368 A1 | 8/2001 |
| WO | WO 01/95810 A2 | 12/2001 |
| WO | WO 02/069808 A2 | 9/2002 |
| WO | WO 03/022164 A2 | 3/2003 |
| WO | WO 03/077767 A1 | 9/2003 |
| WO | WO 2005/060842 A1 | 7/2005 |
| WO | WO 2005/096963 A2 | 10/2005 |
| WO | WO 2006/105283 A2 | 10/2006 |

(56) References Cited

FOREIGN PATENT DOCUMENTS

| WO | WO 2006/121968 A2 | 11/2006 |
|---|---|---|
| WO | WO 2006/121970 A2 | 11/2006 |
| WO | WO 2007/044833 A2 | 4/2007 |

OTHER PUBLICATIONS

ACMI Corporation, "Dolphin II and Destin-U-Flo Fluid Management Systems for Hysteroscopy", ACMI Corporation, 2002 (1 page).
Action Closing Prosecution for 95/002,058 mailed Aug. 9, 2013 (34 pages).
Advisory Action in U.S. Appl. No. 11/929,940 mailed Sep. 10, 2010 (3 pages).
Bacsko "Uterine Surgery by Operative Hysteroscopy", European Journal of Obstetrics & Gynecology and Reproductive Biology, vol. 71, pp. 219-222, 1997 (4 pages).
Baggish et al., "Diagnostic and Operative Hysterectomy," Mosby, pp. 97-105, 123-125, 127-132, 353-355, and 394-398, 1999 (27 pages).
Claim chart for anticipation of claims 1-8 based on Banko US 3,945,375 (4 pages).
Claim chart for anticipation of claims 1-8 based on Kresch US 5,456,689 (4 pages).
Claim chart for anticipation of claims 1-8 based on Savage US 6,032,673 (13 pages).
C.R. Bard, Inc, "The HydroFlex HD System" (1 page).
Cravello et al., "Hysteroscopic Resection of Fibroids: Results with a 6-Year Follow-up Period", Journal of Gynecologic Surgery, vol. 15, No. 1, 1-5 1999 (5 pages).
Defendant Hologic Inc.'s Preliminary, Non-Binding List of Asserted Prior Art References in *Smith & Nephew, Inc.* v. *Hologic, Inc.* Civil Action Nos. 11-CV-12064-RWZ and 10-CV-10951-RWZ, U.S. District Court for the District of Massachusetts, Feb. 8, 2012, (7 pages).
Denial of Order for 95/001,955 mailed Jun. 4, 2012 (5 pages).
Denial of Petition for 95/001,955 mailed Sep. 28, 2012 (5 pages).
Dictionary definition of reciprocate, Merrian-Webster Dictionary, on-line edition, retrieved Mar. 20, 2013 (1 page).
Dictionary definition of rotate, Merriam-Webster Dictionary, on-line edition, retrieved Mar. 20, 2013 (1 page).
Dictionary definition of translate, Merriam-Webster Dictionary, on-line edition, retrieved Mar. 20, 2013 (1 page).
Drews et al., "Surgical Approach to Myomas: Laparoscopy and Hysteroscopy", Seminars in Reproductive Endocrinology, vol. 10, No. 4, pp. 367-377, 1992 (11 pages).
Dumesic et al., "A New Approach to Hysteroscopic Cannulation of the Fallopian Tube", Journal of Gynecologic Surgery, vol. 7, No. 1, pp. 7-9, 1991 (3 pages).
Emanuel et al., "Long-term Results of Hysteroscopic Myomectomy for Abnormal Uterine Bleeding", Obstetrics & Gynecoogy, vol. 93, No. 5, Part I, pp. 743-748, 1999 (6 pages).
European Patent Office Examination Report for Application No. 05 786 521.4-2305 dated Apr. 21, 2010 (4 pages).
European Patent Office Examination Report for Application No. 05 786 521.4-2305 dated Sep. 26, 2010 (5 pages).
Executed Expert Declaration of Dr. Henry A. Dominicis in support of Request for Inter Parties Reexamination of U.S. Patent No. 8,061,359, (150 pages).
Executed Expert Declaration of Hal Walbrink in support of Request for Inter Parties Reexamination of U.S. Patent No. 8,061,359 (22 pages).
Exhibit P To Hologic's Opposition to Smith & Nephew's Motion for Preliminary Injunction, Redacted, *Smith & Nephew, Inc.* v. *Hologic, Inc.* Civil Action No. 11-CV-12064-RWZ, filed Dec. 30, 2011 (99 pages).
First Office Action for 95/002,058 mailed Sep. 19, 2012 (37 pages).
Franchini et al., "Endometrial resection: a diagnostic tool in postmenopausal women", Gynecological Endoscopy, 8, pp. 111-114, 1999 (5 pages).
"From Distention to Deficit Monitoring Taking the All-In-One Approach", W.O.M. World of Medicine (1 page).

Gerber et al., "The Endoscapel: A new endoscopic instrument for supracervical hysterectomy and morcellation of masses; clinical evaluation", European Journal of Obstetrics & Gynecology and Reproductive Biology, 86, p. S12, 1999 (1 page).
Gynecare, "Fluid Management System" Instructions for Use (26 pages).
Gynecare "Motor Drive Unit" Instructions for Use (3 pages).
Gynecare X-Tract, "Tissue Morcellator", Instructions for Use (3 pages).
Gynescope Corporation "Laser Fiber Director", Advertisement, Journal of Gynecologic Surgery, vol. 6, No. 1, 1990 (2 pages).
Hess et al., "Textbook of Bilio-Pancreatic Disease", vol. III, PICCIN, e.g. Fig 6.5.1, pp. 1584-1586, 1997 (5 pages).
Hologic's Opposition to Smith & Nephew's Motion for Preliminary Injunction, Redacted, *Smith & Nephew, Inc.* v. *Hologic, Inc.*, Civil Action No. 11-CV-12064-RWZ, filed Dec. 30, 2011 (26 pages).
"HysteRo-Purator 1143-1 Technical Data" WISAP (2 pages).
International Search Report for International Application No. PCT/US2011/053753 mailed on Dec. 20, 2011 (4 pages).
International Search Report for International Application No. PCT/US2005/029807 mailed on Jun. 13, 2006 (5 pages).
Japanese Office Action in Japanese Patent Application No. 2007-530014, dated Feb. 15, 2011 (10 pages).
Karl Storz, Advertisement, Journal of Gynecologic Surgery, vol. 5, No. 4, 1989 (3 pages).
Karl Storz, "Pilot A Course to Successful Outcomes", Intermetro Industries Corporation, 2001 (2 pages).
Karl Storz "Uterine Resectoscopes for Endometrial Ablation and Resection", Advertisement, Journal of Gynecologic Surgery, vol. 6, No. 1, 1990 (3 pages).
Lin et al. "Clinical Applications of a New Fujinon Operating Fiberoptic Hysteroscope", Journal of Gynecologic Surgery, vol. 6, No. 2, pp. 81-87, 1990 (7 pages).
Mettler et al., "Pelviscopic uterine surgery" Surgical Endoscopy, 6, pp. 23-31, 1992 (9 pages).
Neis et al., "Hysteroscopy: Textbook and Atlas", Thieme Medical Publishers, pp. 91-103, 1994 (13 pages).
Nisolle et al., "Endometrial ablation with the Nd-YAG laser in dysfunctional bleeding" Minimally Invasive Therapy, vol. 1, pp. 35-39, 1991 (5 pages).
Office Action in U.S. Appl. No. 09/486,977 mailed Sep. 7, 2005 (7 pages).
Office Action in U.S. Appl. No. 11/780,759 mailed Jul. 22, 2010 (5 pages).
Office Action in U.S. Appl. No. 11/780,759 mailed Jul. 26, 2010 (7 pages).
Office Action in U.S. Appl. No. 11/780,759 mailed Jan. 5, 2011 (7 pages).
Office Action in U.S. Appl. No. 11/929,938 mailed Jul. 30, 2010 (10 pages).
Office Action in U.S. Appl. No. 11/929,938 mailed Jan. 5, 2011 (10 pages).
Office Action in U.S. Appl. No. 11/929,940 mailed Dec. 30, 2009 (9 pages).
Office Action in U.S. Appl. No. 11/929,940 mailed Jul. 1, 2010 (12 pages).
Office Action in U.S. Appl. No. 95/001,933 mailed Jun. 5, 2012 (37 pages).
Office Action in U.S. Appl. No. 95/001,933 mailed Apr. 1, 2013 (94 pages).
Office Action in U.S. Appl. No. 95/001,933 mailed Sep. 19, 2013 (79 pages).
Olympus Product Catalogue: Part No. A2461—OP Nephroscope, Sep. 1991 (3 pages).
Opening Claim Construction Brief of Defendant Hologic, Inc., from Massachusetts Civil Action No. 1:11-cv-12064-RWZ (Defendant's Opening Markman Brief.) (24 pages).
Opening Markman Brief of Plaintiff Smith & Nephew, Inc., from Massachusetts Civil Action No. 1:11-cv-12064-RWZ "Plaintiff's Opening Markman Brief") (24 pages).
Order Granting Request for Reexam 95/001,933, mailed Jun. 5, 2012 (29 pages).

(56) References Cited

OTHER PUBLICATIONS

Park et al., "Endoscopic Management of Uterine Myoma", Yonsei Medical Journal, vol. 40, No. 6, pp. 583-588, 1999 (6 pages).
Patent Owner's Aug. 3, 2012 Response to Office Action for U.S. Appl. No. 95/001,933 mailed Jun. 5, 2012 (151 pages).
Patent Owner's Jun. 3, 2013 Response to Office Action for U.S. Appl. No. 95/001,933 mailed Apr. 1, 2013 (75 pages).
Patent Owner's Oct. 21, 2013 Response to Action Closing Prosecution in 95/001,933 mailed Sep. 19, 2013 (218 pages).
Patent Owner's Jan. 22, 2013 Response to Office Action for 95/002,058 mailed Sep. 9, 2012 (379 pages).
Patent Owner's Sep. 9, 2013 Response to Action Closing Prosecution for 95/002,058 dated Aug. 9, 2013 (7 pages).
Patent Owner's Oct. 25, 2010 Response to Office Action for U.S. Appl. No. 11/780,759 mailed Jul. 26, 2010 (13 pages).
Patent Owner's Mar. 31, 2011 Response to Office Action for U.S. Appl. No. 11/780,759 mailed Jan. 5, 2010 (15 pages).
PCT International Preliminary Report on Patentability for Application No. PCT/US2005/029807 dated Feb. 28, 2007, (9 pages).
Petition for Review for 95/001,955, Jul. 3, 2012 (36 pages).
Reexam Order for 95/002,058 mailed Sep. 19, 2012 (54 pages).
Reexamination Litigation Search Report CRU 3999 filed Apr. 2, 2012 in U.S. Appl. No. 95/001,955 (33 pages).
Reference AQ "Fishing Reel produced and sold by Shimano of Japan in to the U.S. prior to Oct. 26, 2001," as cited in the IDS filed Oct. 17, 2005 in the prosecution file history of U.S. Appl. No. 09/983,810 (7 pages).
Request for Inter Partes Reexamination of U.S. Patent No. 8,061,359, filed Apr. 2, 2012 (265 pages).
Richard Wolf "Morce-Power 2306 Electronic Morcellator" (2 pages).
Richard Wolf "The Fluid Manager" (2 pages).
Right of Appeal Notice mailed Jan. 14, 2014 for U.S. Appl. No. 95/001,933 (58 pages).
Right of Appeal Notice mailed Feb. 4, 2015 for U.S. Appl. No. 95/002,058 (35 pages).
Second Office Action for 95/002,058 mailed Jan. 24, 2014 (31 pages).
Sheath et al., "Fiberoptic Light for Oophorectomy at Vaginal Hysterectomy", Journal of Gynecologic Surgery, vol. 14, No. 3, pp. 119-122, 1998 (4 pages).
Sugimoto "A Color Atlas of Hysteroscopy" Springer-Verlag Tokyo, 1999 (17 pages).
Third Party Response to Office Action for U.S. Appl. No. 95/001,933 mailed Apr. 1, 2013 (101 pages).
Third Party Response to Office Action for U.S. Appl. No. 95/001,933 mailed Jun. 5, 2012 (777 pages).
Third Party Response in 95/001,933 to Action Closing Prosecution mailed Sep. 19, 2013 (38 pages).
Third Party Response to First Office Action for 95/002,058 mailed on Sep. 19, 2012.
Third Party Response in 95/002,058 to Action Closing Prosecution mailed Apr. 1, 2013 (101 pages).
Third Party Response in 95/002,058 to Action Closing Prosecution mailed Aug. 9, 2013 (25 pages).
Valle "Hysteroscopic Removal of Submucous Leiomyomas", Journal of Gynecologic Surgery, vol. 6, No. 1, pp. 89-96, 1990 (9 pages).
Weck "A Direct Path to Diagnostic and Operative Control: The Weck-Baggish Hysteroscopy System" Advertisement, Journal of Gynecologic Surgery, vol. 7, No. 1, 1991 (2 pages).
Williamson et al., Editorial 1 "Complications of hysteroscopic treatments of menorrhagia", British Journal of Anesthesia, vol. 77, No. 3, pp. 305-308, 1996 (4 pages).

* cited by examiner

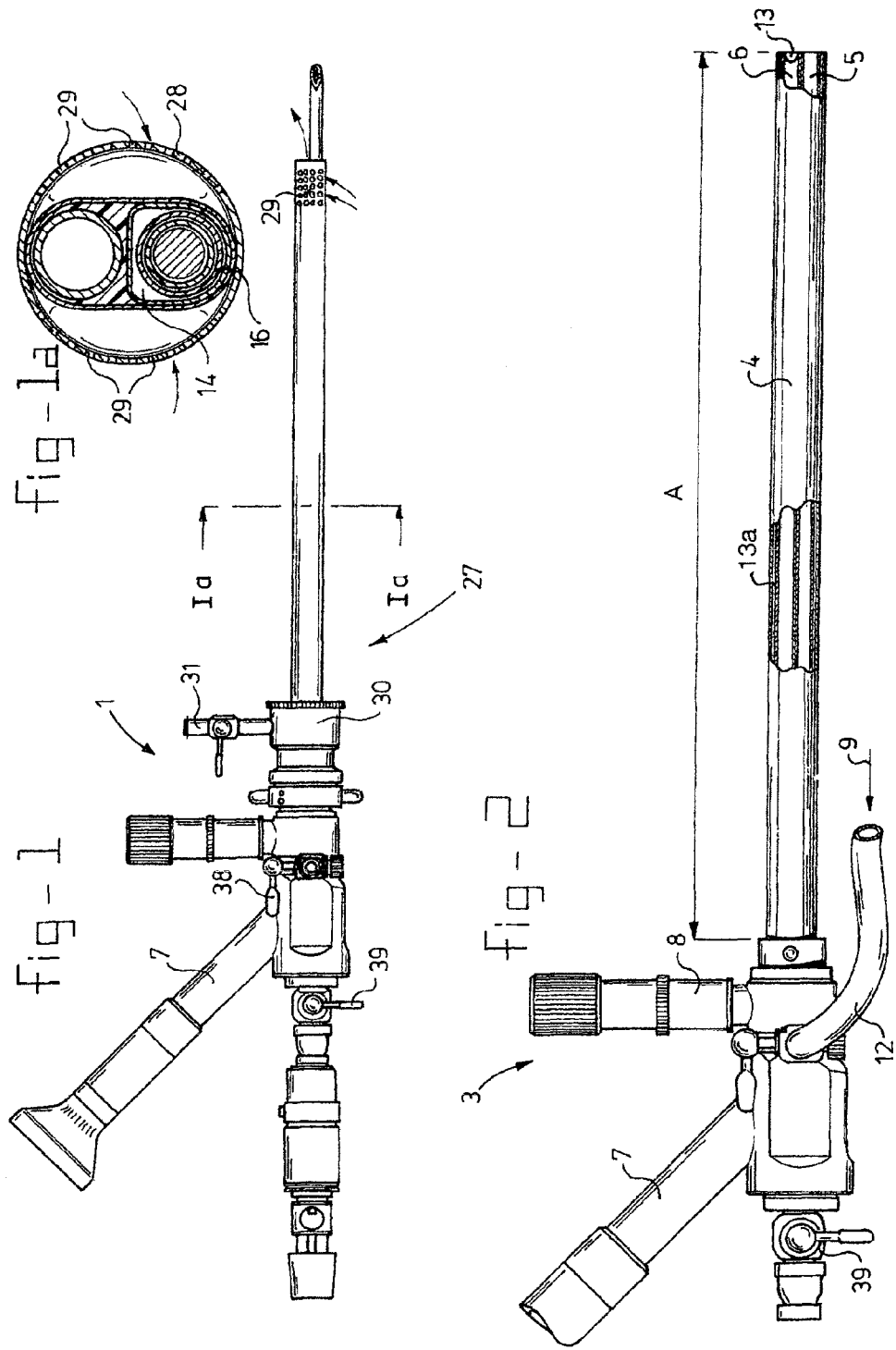

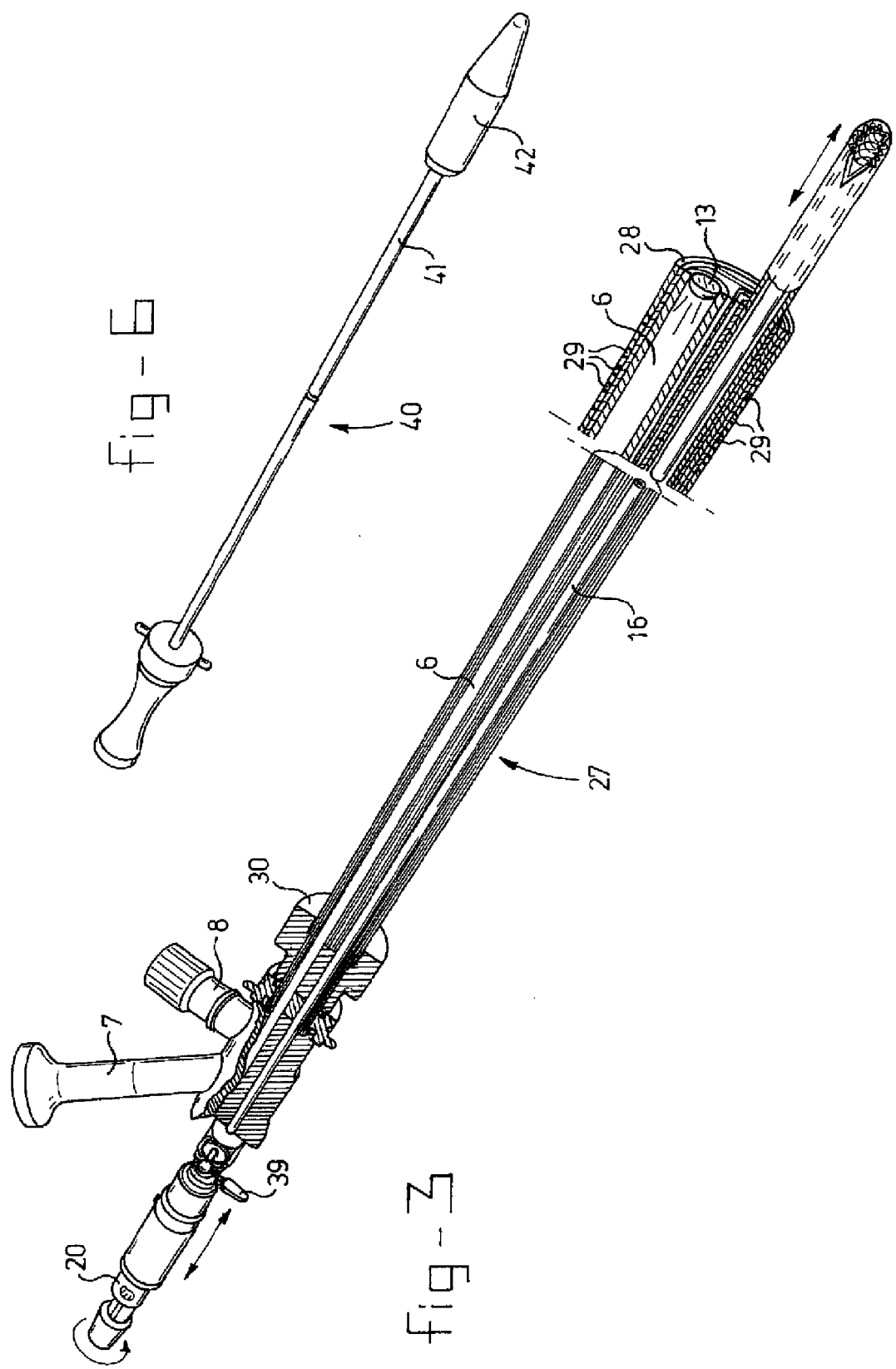

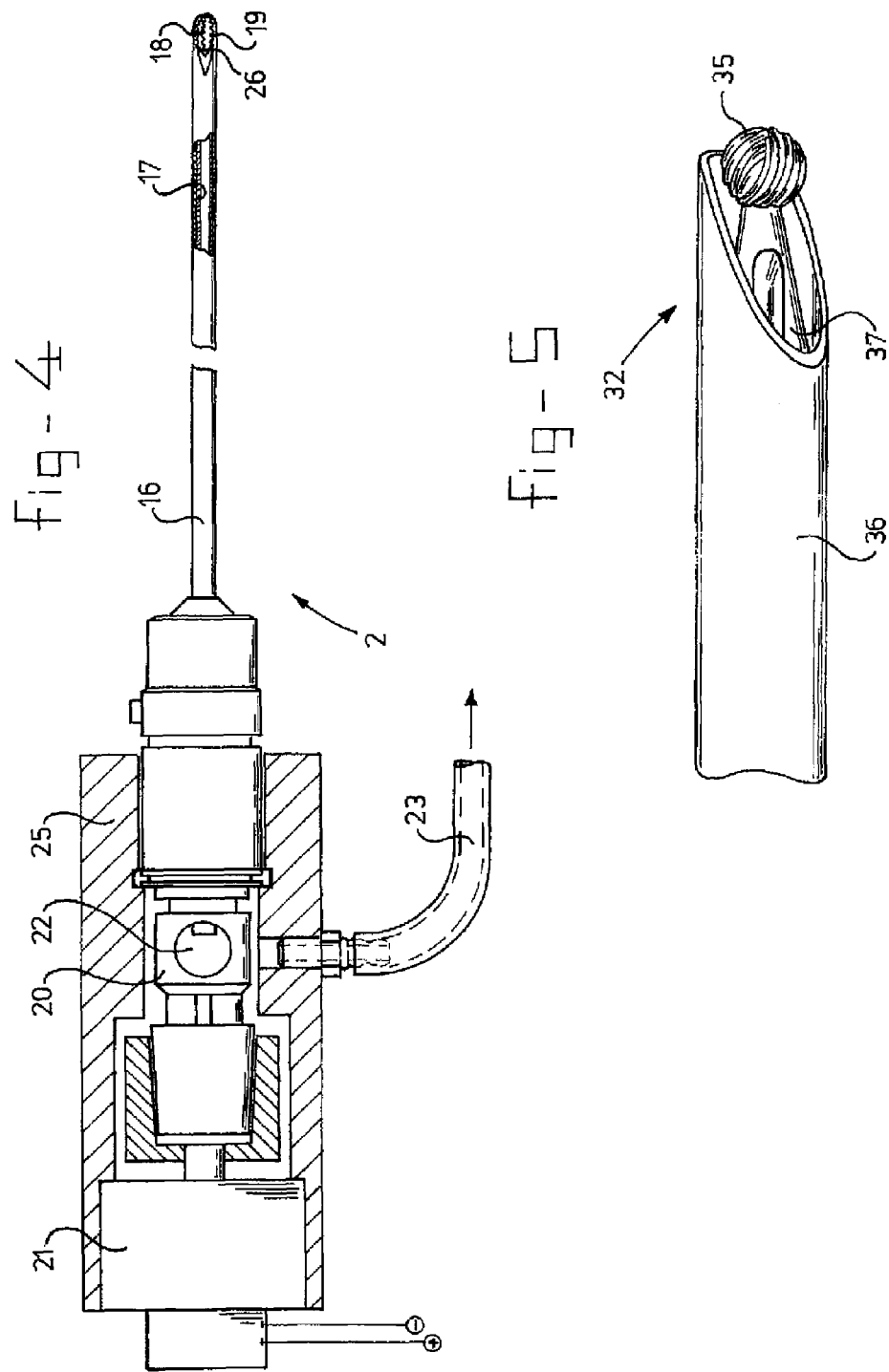

SURGICAL CUTTING DEVICE AND METHOD FOR ITS USE

CROSS-REFERENCE TO RELATED APPLICATIONS

This application is a continuation of prior application Ser. No. 11/929,940, filed on Oct. 30, 2007, which is a divisional of prior application Ser. No. 11/780,759, filed on Jul. 20, 2007, which is a continuation of application Ser. No. 09/486,977, filed on Mar. 6, 2000, which was the National Stage of International Application No. PCT/NL98/00504, filed Sep. 4, 1998, which claims the benefit of and priority to Netherlands Application No. 1006944, filed Sep. 4, 1997, each of the above applications is hereby incorporated by reference herein in its entirety.

FIELD OF THE INVENTION

The present invention relates to a surgical endoscopic cutting device.

BACKGROUND OF THE INVENTION

Surgical cutting devices are generally known and used for the removal of hard and/or soft tissue, such as in the vicinity of the knee joint. Such cutting devices are used in, for example, a joint cavity, where they can be guided endoscopically by separately inserting a viewing device having a light source and an observation portion. Such operations are successfully used in organs and joints lying not too deep underneath the skin.

When operations are being carried out on organs lying deeper, other techniques are currently used. If, for example, tissue has to be removed from the uterus, prostate, or urinary bladder, such as mucous membrane or other tissues, it was customary until now to use a so-called "loop." This is a loop-shaped cutting wire which is brought to a first potential, while the wall of the uterus is brought to a second, different potential. Tissue is removed by moving the loop along the uterus wall. In order to be able to carry out such an operation, it is necessary to dilate the uterus. Dilation is carried out by introducing a fluid. In order to maintain the effect of the potential difference, a non-conducting fluid is used, for example a 5% sorbitol solution. Because wounds are caused during the treatment described above, a good part of this fluid is resorbed into the patient's bloodstream (by way of the uterus). This can lead to highly dangerous electrolyte displacements. It has been found that the tissue can be removed more easily by working with a high-frequency monopolar electric current, but there is a risk of high-frequency electric current leading to internal and external burns. The loop is generally fitted on an endoscope and moved back and forth along the uterus wall with the endoscope. The tissue cut off during this treatment has to be removed from the uterus, which considerably extends the duration of the operation. Furthermore, the doctor has to check that all detached material actually has been removed.

This means that such operations are very time-consuming and require the surgeon to repeatedly move the device back and forth. This is tiring and consequently difficult to learn. Moreover, the patient has to be monitored continually during the operation, in order to prevent the undesirable phenomena described above. It is not uncommon for such an operation to be broken off because the patient's life is endangered by the side effects.

On the other hand, it is desirable to be able to carry out such operations instead of simply performing a hysterectomy.

WO 96/11638 discloses a cutter including a hollow stem and a cutting head accommodated inside a rigid housing. This rigid housing likewise contains a viewing channel with the necessary optics. U.S. Pat. No. 5,195,541 describes a laparoscopic discectomy apparatus. For a laparoscopic method it is essential to inflate the related cavity using gas. The gas feed is discontinuous and has no effect on viewing of the operation site.

Fluid is introduced by way of a space between the stem and the rigid housing and discharged together with the detached tissue through the hollow stem of the cutter.

This device could be satisfactory for the removal of tissues from certain body cavities, such as from the bladder. However, in the case of other body cavities, it is necessary to "blow up" the cavity before treatment can be carried out. An example of this is the uterus, in which it is important that the amount of enlargement of the organ be accurately controlled. The irregular discharge of fluid through the hollow stem of the cutter, caused partly by the irregular release of tissue, means that it cannot be guaranteed that the pressure inside the cavity is accurately controlled.

Such a device is consequently not very suitable for use in the treatment of such a cavity.

SUMMARY OF THE INVENTION

The object of the present invention is to provide a device which can perform such a treatment.

According to the invention, a further outlet channel is provided, the function of which is independent of whether or not detached tissue has been released. In other words, a regular discharge of fluid can occur through this further outlet channel. Since only a minor part of the fluid is now discharged through the outlet, in which there are detached pieces of tissue, the pressure inside the body cavity can be regulated and controlled accurately. This makes it possible to remove undesired tissue from cavities such as the uterus. The applicability of the removal of tissues by cutting is consequently considerably increased.

The further outlet channel described above is formed by an insertion tube fitted around the endoscopic device. This insertion tube serves to clear a space for the endoscopic device. For this purpose, the front side of the insertion tube can be provided with an insertion mandrel, which is removed after the positioning of the insertion tube and replaced by the endoscopic device described above. In this case the further outlet channel can be defined between the endoscopic device and the insertion tube.

In the case of such a construction it is desirable for a coupler to be present to provide a coupling between the rigid housing and the insertion tube described above.

Discharge of the tissue material which has been detached can be achieved either by making the stem on which the cutting elements are fitted hollow, or by fitting a protective tube around the cutter. Such a protective tube can also be used without the space between protective tube and stem serving as an outlet channel. This means that the cutter can be designed as a separate unit which can be coupled to the rigid housing, which has advantages in particular for purposes of sterilization. Namely, the device can then be detached in a simple way.

For the removal of tissue from a uterus it is essential for the rigid housing to have a length which is sufficient to reach all tissue parts, i.e. a length of at least 30 cm.

The observation part of the device described above includes a light channel in the housing, provided near one end with a lens and near the other end with an observation mechanism. The latter can include an eyepiece or a connection for a camera so that the surgeon can carry out the operation using a monitor and others can possibly look at the same time.

The cutting elements described above can include any cutting element known in the prior art. In other words, a cutting head with cutting faces can be used, but it is also possible to use constructions with teeth, meshing with the protective tube or otherwise. In the latter instance, the protective tube is preferably provided with a lateral opening through which a part of the cutting elements extends so that on each revolution, part of the tissue is removed and can be discharged directly through the interior of the drive/discharge tube of the cutter.

The invention also relates to a method for the removal of uterus tissue in which the device described above is used. In other words, a machining operation is now applied with the use of a physiological fluid which can be electrically conducting without any problem, while at the same time the removed tissue is sucked out. It is, of course, possible to suck out the tissue at a later stage. The machining operation is carried out by a rotating action.

According to a further embodiment of the method, an outlet and a further outlet are present, and the pressure inside the body cavity is regulated by metering the quantity of fluid which moves through the further outlet. The insertion of the surgical endoscopic cutting device is preferably carried out in the manner described above using an insertion mandrel and insertion tube.

BRIEF DESCRIPTION OF DRAWINGS

The invention will be explained in greater detail below with reference to an exemplary embodiment shown in the drawings, in which:

FIG. 1 shows the endoscopic cutting device according to the invention in the assembled state, in side view and partially in section;

FIG. 1a shows the viewing/receiving part of the cutting device of FIG. 1 in section along the line Ia-Ia;

FIG. 2 shows a side and partially cut-away view of the viewing/receiving part of the cutting device of FIG. 1;

FIG. 3 shows a partially cut-away perspective view of the device of FIG. 1, with the insertion end enlarged;

FIG. 4 shows a partially sectional side view of the cutter of the cutting device of FIG. 3;

FIG. 5 shows a variant of the cutter shown in FIG. 4; and

FIG. 6 shows an insertion mandrel according to the invention.

DETAILED DESCRIPTION

The endoscopic cutting device according to the invention is indicated in its entirety by 1 in FIG. 1. It comprises a viewing/receiving part 3, which is shown in FIG. 2, a cutting part 2, which is shown in greater detail in FIGS. 4 and 5, and an insertion mandrel, which is shown in FIG. 6.

With reference to FIG. 2, it can be seen that the viewing/receiving part 3, is composed of an outer tube 4 in which a main channel 5 and viewing channel 6 are defined. Viewing channel 6 ends at one side in a lens 13 and at the other side in a viewing tube 7, on which an eyepiece or camera connection is placed. A connection 8 for a light source is also present, for connection to a light guide, such as a fibre optics bundle 13a, which provides for lighting at the end of lens 13. Near the control end, tube 4 is provided with a fluid inlet 9 connected to a hose 12, for adding a physiological salt solution.

A shut-off valve is indicated by 39.

The length of the actual outer tube 4, is indicated by A and is more than 30 cm.

FIG. 4 shows details of the cutter or the cutting part 2, which is composed of a protective tube 16 inside of which a drive/suction tube 17 is fitted. Near the working end, tube 17 is provided with teeth 19 which mesh with teeth 18 provided in an opening 26 in the end part of protective tube 16. Near the other end, drive/suction tube 17 is provided with a coupling 20, which can be connected at one end to a rotating drive motor 21, not shown in detail, and at the other end is provided with an opening 22 through which fluid and removed material can be discharged by way of suction tube 17 to the discharge hose 23. A pressure regulator can be present in this discharge hose 23, which is connected to a vacuum source.

In FIG. 1 the insertion part is indicated by 27. This insertion part is composed of an insertion tube 28 which is provided with openings 29 at one end and near the other end, the insertion part 27 is provided with a bayonet connection 30 and an outlet 31. Insertion tube 28 is designed in such a way that tube 4 can be fitted therein, as shown in FIGS. 1 and 3, while it is also possible to fit insertion mandrel 40, provided with stem 41 and mandrel 42, in insertion tube 28

The construction described above has an inlet 38 for fluid. Inlet 38 extends to channel 14 (FIG. 1a), i.e. the space bounded between the outer tube 4 and the protective tube 16 and 36, respectively from FIG. 4 or 5. A shut-off valve 39, which is connected to channel 14, is present, while the further outlet is indicated by 31. A discharge hose 23 for tissue and fluid is shown. During the removal of tissue, with a substantially continuous supply of fluid through inlet 38, some of the fluid will be discharged through outlet 23. This relatively small amount will be mixed with a mixture released during the cutting operation. Most of the fluid will be discharged through the further outlet 31. This discharge is unimpeded and occurs through openings 29. Pressure variations occurring due to the presence or absence of removed tissue in channel 17 (FIG. 4) have little or no influence on the pressure inside the body cavity owing to the presence of the further outlet 31.

If the device is to be inserted into, for example, a uterus, insertion mandrel 40 will first be inserted, with shut-off valve 39 open, into insertion tube 28 with bayonet 30. This assembly is then placed in the uterus in a relatively simple manner due to the shape of mandrel 42. Mandrel 42 is then removed by manipulating stem 41, and the construction shown in FIG. 2 is placed in tube 28. Connection is made here to bayonet 30. The cutting action can then begin after the uterus has been dilated by the introduction of fluid. This fluid can be a physiological flushing and distension fluid, such as a physiological salt solution (NaCl 0.9%). In the event of the (unavoidable) resorption of the physiological fluid into the blood, electrolyte displacement, with fatal consequences for the patient, will not occur. Owing to the absence of electrical current, the burns described above are also ruled out.

By switching on motor 21, tube 17 is set in rotation and teeth 19 move regularly along cutting edge 18 of protective tube 16 which remains stationary. While they are moving along each other and picking up tissue material between them, a cutting, detaching action on the tissue material is occurring. The cut, detached material is removed through the interior of tube 17 and outlet 23.

The appropriate area of the uterus can be treated by moving parts 18 and 19 along the uterus wall or along tissue to be removed, which can be observed through viewing tube 7 by supplying light through connection 8.

Through the use of a continuous flow system, a constantly clear view is obtained for the observer even if blood and/or mucous is/are in the mixture. Moreover, the pressure can be maintained as low as possible, in order to prevent intravasation.

FIG. 5 shows a variant of the end of the cutter. The cutter or cutting part are indicated in their entirety by 32. The protective tube is indicated by 36 and is beveled near the end. The drive/suction tube is indicated by 37 and provided with a cutting head near the end. In this embodiment, there is either no interaction between cutting head 35 and protective tube 36, or head 35 and tube 36 interact near the edge of tube 36, which is adapted for that purpose by grinding.

It is understood that such cutting elements can be designed in any way known in the prior art.

These and further modifications are considered to lie within the scope of the present application, to be immediately obvious to the person skilled in the art after reading the description, and to lie within the scope of the appended claims. For instance, it is possible to effect the supply of working fluid and the discharge of cleaning material in another way, i.e., to arrange the interior of housing 4 slightly differently. Furthermore, the method described above can be used for the removal of other tissue material, such as prostate tissue through the urethra, or for the removal of tissue from the wall of the urinary bladder.

What is claimed is:

1. A method for removal of tissue from a uterus, comprising:
    transcervically inserting a distal region of an endoscope into the uterus, the endoscope including an inlet valve and an elongated member comprising discrete channels extending from a proximal region of the elongated member to the distal region, a first of the discrete channels having a proximal end in communication with the inlet valve such that fluid from the inlet valve is able to flow into and through the first discrete channel to the uterus, and a second of the discrete channels having an observation mechanism at a proximal end thereof and a lens adjacent to a distal end thereof, the second discrete channel being sealed from the first discrete channel to prevent the fluid from the inlet valve from entering the uterus through the second discrete channel;
    inserting a motor driven cutter into the first discrete channel such that a distal cutting region of the motor driven cutter extends distally beyond the endoscope in the uterus;
    delivering the fluid into the uterus through the inlet valve and the first discrete channel to distend the uterus;
    energizing an electric motor to drive the motor driven cutter to cut and detach the tissue from the uterus; and
    aspirating the cut and detached tissue and at least a portion of the fluid from the uterus through the cutter.

2. The method of claim 1, wherein the inserted motor driven cutter includes an outer tube defining a cutting window at a distal region thereof and an inner tube received within the outer tube.

3. The method of claim 2, wherein the energizing causes the inner tube to rotate relative to the outer tube to cut the tissue.

4. The method of claim 3, wherein the inner tube has a cutting element at a distal region thereof that cuts the tissue at the cutting window.

5. The method of claim 1, wherein the endoscope includes a tube defining a lumen, the elongated member being positioned at least partially within the lumen.

6. The method of claim 5, further comprising discharging at least a portion of the fluid from the uterus through the tube.

7. The method of claim 6, wherein the at least a portion of the fluid discharged through the tube is discharged from the uterus between the elongated member and the tube.

8. The method of claim 7, further comprising controlling pressure within the uterus.

9. The method of claim 1, wherein the transcervically inserting the distal region of the endoscope into the uterus includes (i) transcervically inserting an insertion tube coupled with an insertion mandrel into the uterus, (ii) removing the insertion mandrel from the insertion tube, and (iii) inserting the distal region of the endoscope into the insertion tube.

10. The method of claim 1, wherein the fluid is a physiological salt solution.

11. The method of claim 1, wherein the tissue is a fibroid.

12. The method of claim 1, wherein the transcervically inserting the distal region of the endoscope occurs prior to the inserting the motor driven cutter.

13. A method for removal of tissue from a uterus, comprising:
    transcervically inserting a distal region of an endoscope into the uterus, the endoscope including a port for receiving a motor driven cutter and an elongated member having a first discrete channel and a second discrete channel, the first and the second discrete channels both extending from a proximal region of the elongated member to a distal region of the elongated member, the first discrete channel having a straight, central longitudinal axis extending from the port to an opening at a distal tip of the endoscope, and the second discrete channel having an observation mechanism at a proximal end thereof and a lens adjacent to a distal end thereof;
    inserting the motor driven cutter into the first discrete channel through the port, the motor driven cutter for cutting and detaching the tissue;
    introducing fluid into the uterus; and
    aspirating at least a portion of the fluid with the cut and detached tissue from the uterus through a lumen of the motor driven cutter.

14. The method of claim 13, wherein the inserted motor driven cutter includes an outer tube defining a cutting window at a distal region thereof and an inner tube received within the outer tube.

15. The method of claim 14, further comprising rotating the inner tube relative to the outer tube to cut and detach the tissue.

16. The method of claim 15, wherein the inner tube has a cutting element at a distal region thereof that cuts and detaches the tissue at the cutting window.

17. The method of claim 13, wherein the endoscope includes a tube defining a lumen, the elongated member being positioned at least partially within the lumen.

18. The method of claim 17, further comprising discharging at least a portion of the fluid from the uterus through the tube.

19. The method of claim 18, wherein the at least a portion of the fluid discharged through the tube from the uterus is discharged between the elongated member and the tube.

20. The method of claim 19, further comprising controlling pressure within the uterus.

21. The method of claim 13, wherein the transcervically inserting the distal region of the endoscope into the uterus includes (i) transcervically inserting an insertion tube coupled with an insertion mandrel into the uterus, (ii) removing the insertion mandrel from the insertion tube, and (iii) inserting the distal region of the endoscope into the insertion tube.

22. The method of claim 13, wherein the fluid is a physiological salt solution.

23. The method of claim 22, wherein the tissue is a fibroid.

24. The method of claim 13, wherein the transcervically inserting the distal region of the endoscope occurs prior to the inserting the motor driven cutter.

25. The method of claim 13, wherein the second discrete channel is sealed from the first discrete channel to prevent the fluid from entering the uterus through the second discrete channel.

26. The method of claim 13, wherein the introducing the fluid into the uterus distends the uterus.

* * * * *